(12) United States Patent
Stahmann et al.

(10) Patent No.: US 7,935,936 B2
(45) Date of Patent: May 3, 2011

(54) METHOD AND APPARATUS FOR RADIATION EFFECTS DETECTION

(75) Inventors: Jeffrey E. Stahmann, Ramsey, MN (US); William J. Linder, Golden Valley, MN (US); Scott R. Stubbs, Maple Grove, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 274 days.

(21) Appl. No.: 12/361,935

(22) Filed: Jan. 29, 2009

(65) Prior Publication Data
US 2009/0189082 A1   Jul. 30, 2009

Related U.S. Application Data

(60) Provisional application No. 61/024,820, filed on Jan. 30, 2008.

(51) Int. Cl.
*G01T 1/00* (2006.01)
(52) U.S. Cl. .................... 250/394; 250/370.07; 250/395
(58) Field of Classification Search ............. 250/370.01, 250/370.07, 394, 395
See application file for complete search history.

(56) References Cited

U.S. PATENT DOCUMENTS

| | | | |
|---|---|---|---|
| 4,213,045 A | 7/1980 | Fraass et al. |
| 4,678,916 A | 7/1987 | Thomson |
| 4,788,581 A | 11/1988 | Knoll et al. |
| 4,976,266 A | 12/1990 | Huffman et al. |
| 5,059,801 A | 10/1991 | Burgess |
| 5,117,113 A | 5/1992 | Thomson et al. |
| 5,332,903 A | 7/1994 | Buehler et al. |
| 5,572,027 A | 11/1996 | Tawil et al. |
| 5,621,238 A | 4/1997 | Dodd et al. |
| 5,739,541 A | 4/1998 | Kahilainen |
| 5,929,448 A | 7/1999 | Zimmerman |
| 6,532,389 B1 | 3/2003 | Shahandeh |
| 6,718,203 B2 | 4/2004 | Weiner et al. |

(Continued)

FOREIGN PATENT DOCUMENTS
| | | |
|---|---|---|
| WO | WO-02/09775A2 | 2/2002 |
| WO | WO-03/062855A1 | 7/2003 |
| WO | WO-2009/099556A2 | 8/2009 |

OTHER PUBLICATIONS

"International Application Serial No. PCT/US2009/000598, International Search Report mailed Aug. 20, 2009", 4 pgs.

(Continued)

*Primary Examiner* — David P. Porta
*Assistant Examiner* — Mark R Gaworecki
(74) *Attorney, Agent, or Firm* — Schwegman, Lundberg & Woessner, P.A.

(57) ABSTRACT

This document discusses, among other things, an implantable apparatus comprising a plurality of solid state electronic circuits disposed at a plurality of different locations in the apparatus, a plurality of ionizing radiation exposure sensors disposed at the different locations and configured to generate an indication of a non-single-event-upset (non-SEU) effect to the solid state electronic circuit from an exposure to ionizing radiation, wherein the ionizing radiation exposure sensors respectively monitor at least two different types of operating parameters of respectively correspondingly located solid state circuits, and a controller circuit communicatively coupled to the ionizing radiation exposure sensors, wherein the controller circuit is configured to quantify the effect to the solid state electronic circuits using the different monitored operating parameters.

27 Claims, 6 Drawing Sheets

U.S. PATENT DOCUMENTS

| | | |
|---|---|---|
| 6,778,857 B1 | 8/2004 | Montgomery et al. |
| 6,795,730 B2 | 9/2004 | Connelly et al. |
| 6,925,328 B2 | 8/2005 | Foster et al. |
| 6,950,703 B1 | 9/2005 | Shahandeh |
| 6,963,770 B2 | 11/2005 | Scarantino et al. |
| 6,963,771 B2 | 11/2005 | Scarantino et al. |
| 6,969,859 B2 | 11/2005 | Klaasen et al. |
| 7,047,074 B2 | 5/2006 | Connelly et al. |
| 2003/0036776 A1 | 2/2003 | Foster et al. |
| 2005/0216063 A1 | 9/2005 | Hoyme et al. |
| 2006/0224064 A1 | 10/2006 | Clement et al. |
| 2006/0253009 A1 | 11/2006 | Stubbs et al. |
| 2006/0253158 A1 | 11/2006 | Stubbs et al. |
| 2006/0253163 A1 | 11/2006 | Stubbs et al. |
| 2007/0150010 A1 | 6/2007 | Stubbs et al. |

OTHER PUBLICATIONS

"International Application Serial No. PCT/US2009/000598, Written Opinion mailed Aug. 20, 2009", 7 pgs.

Batignani, G., et al., "Functional Characterization of a High-Gain BJT Radiation Detector", *IEEE Transations on Nuclear Science*, 52(5), (2005), 1882-1886.

Fleetwood, D. M., et al., "Total Ionizing Dose Effects on MOS and Bipolar Devices in the Natural Space Radiation Environment", (1998), 9 pgs.

Marbach, J. R., et al., "Management of radiation oncology patients with implanted cardiac pacemakers: Report of AAPM Task Group No. 34", *Med. Phys.*, 21(1), (Jan. 1994), 85-90.

Quertermous, T., et al., "Pacemaker Failure Resulting from Radiation Damage", *Radiology*, 148(1), (Jul. 1983), 257-258.

METHOD AND APPARATUS FOR RADIATION EFFECTS DETECTION

RELATED APPLICATIONS

This application claims the benefit under 35 U.S.C. 119(e) of U.S. Provisional Patent Application Ser. No. 61/024,820, filed on Jan. 30, 2008, which is incorporated herein by reference in it entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices can include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

OVERVIEW

Patients with CFM devices can be exposed to radiation after an implant procedure. The patients can have co-morbidities that require diagnostic x-rays (e.g., a computed tomography, or CT, scan) or radiation therapy (e.g., as a cancer treatment). As medical technology continues to improve, patients with IMDs will live longer and the likelihood that they could become exposed to such radiation increases. The radiation can induce changes in an implanted CFM device that can negatively impact its operation.

This document relates generally to systems, devices, and methods for monitoring hemodynamic parameters of a patient or subject. In example 1, an apparatus includes a solid state electronic circuit and a sensor. The sensor is configured to detect an exposure of the solid state electronic circuit to ionizing radiation, and generate an indication of a non-single-event-upset (non-SEU) effect to the solid state electronic circuit from the exposure to ionizing radiation.

In example 2, the apparatus of example 1 optionally includes a controller circuit communicatively coupled to the ionizing radiation exposure sensor. The controller circuit is configured to quantify the effect to the solid state electronic circuit from the indication generated by the ionizing radiation exposure sensor.

In example 3, the controller circuit of examples 1 and 2 is optionally configured to alter operation of the apparatus according to the indication of the non-SEU effect.

In example 4, the apparatus of examples 1-3 includes a plurality of solid state electronic circuits configured to perform different functions at a plurality of different locations in the apparatus, and a plurality of ionizing radiation exposure sensors disposed at the different locations. The controller circuit is configured to inhibit or deactivate a function of the apparatus when an ionizing radiation exposure sensor indicates a permanent non-SEU effect to the solid state electronic circuit at a location corresponding to the function.

In example 5, the apparatus of examples 1-4 optionally includes a comparison circuit communicatively coupled to the ionizing radiation exposure sensor and the controller circuit, wherein the ionizing radiation exposure sensor includes a test transistor, and wherein the controller circuit is configured to alter operation of the apparatus if the comparison circuit indicates a shift in an operating curve of the test transistor after exposure to radiation.

In example 6, the test transistor of examples 1-5 optionally comprises a test field effect transistor (FET), and wherein the comparison circuit is configured to indicate a shift in drain-source current for a specified gate-source voltage applied to the test FET.

In example 7, the apparatus of examples 1-6 optionally includes a comparison circuit communicatively coupled to the ionizing radiation exposure sensor and the controller circuit, wherein the ionizing radiation exposure sensor includes a test junction diode, and wherein the controller circuit is configured to alter operation of the apparatus if the comparison circuit indicates a shift in an operating curve of the test junction diode after exposure to radiation.

In example 8, the ionizing radiation exposure sensor of examples 1-7 optionally includes a test amplifier circuit that includes a bipolar junction transistor. The comparison circuit is optionally configured to indicate a shift in signal gain of the test amplifier circuit for a specified input signal applied to the amplifier circuit.

In example 9, the apparatus of examples 1-8 optionally include a plurality of solid state electronic circuits disposed at a plurality of different locations in the apparatus and a plurality of ionizing radiation exposure sensors disposed at the different locations. The ionizing radiation exposure sensors include different circuit structures to monitor different operating parameters, and wherein the controller circuit is configured to quantify the effect to a solid state electronic circuit using the different monitored operating parameters.

In example 10, the radiation exposure sensors of examples 1-9 optionally include at least one of: a PN junction diode test circuit, a schottky junction diode test circuit, an N-channel FET test circuit, a P-channel FET test circuit, an NPN bipolar junction transistor test circuit, and a PNP bipolar junction transistor test circuit.

In example 11, the sensor of examples 1-10 optionally comprises an accumulated ionizing radiation exposure sensor configured to generate the indication of a non-SEU effect to the solid state electronic circuit from the solid state electronic circuit's accumulated exposure to ionizing radiation.

In example 12, the apparatus of examples 1-11 optionally includes an ionizing radiation dose rate sensor communicatively coupled to the controller circuit, and wherein the controller circuit is configured to blank the indication from the accumulated ionizing radiation exposure sensor when the radiation dose rate sensor indicates that flux ionizing radiation exceeds a flux ionizing radiation threshold.

In example 13, the sensor of examples 1-12 optionally comprises an ionizing radiation dose rate sensor configured to generate the indication of a non-SEU effect to the solid state electronic circuit from the solid state electronic circuit's exposure to flux ionizing radiation that exceeds a flux ionizing radiation threshold.

In example 14, the apparatus of examples 1-13 optionally comprises a cardiac function management (CFM) device, and wherein the controller circuit is configured to blank any sensing features of the CFM device when the ionizing radiation dose rate sensor detects high flux ionizing radiation.

In example 15, the ionizing radiation dose rate sensor of examples 1-14 optionally includes at least one of a junction diode or a bipolar junction transistor.

In example 16, the apparatus of examples 1-15 optionally comprises a CFM device, The controller circuit is optionally configured to, according to the indication of the non-SEU effect, transition the CFM device to a mode that provides pacing therapy to a ventricle when a V-V interval exceeds a specified ventricular interval without timing the pacing of the ventricle from an atrial cardiac event, and that provides pacing therapy without regard to any intrinsic cardiac depolarization event occurring in the ventricle.

In example 17, the apparatus of examples 1-16 optionally includes a read only memory (ROM) communicatively coupled to the controller circuit, and wherein the controller circuit is configured to, according to the indication of the non-SEU effect, transition the apparatus to a mode where the controller circuit only performs program instructions that are included in the ROM.

In example 18, the apparatus of examples 1-17 optionally includes a reset circuit communicatively coupled to the controller circuit, and wherein the controller circuit is configured to initiate a reset to the apparatus according to the indication of the non-SEU effect.

In example 19, the solid state electronic circuit of examples 1-18 optionally comprises an integrated circuit (IC). The ionizing radiation exposure sensor is optionally configured to indicate a shift in a first operating parameter of the IC, and the controller circuit is optionally configured to modify a second operating parameter of the IC to accommodate the shift in the first operating parameter.

In example 20, the apparatus of examples 1-19 optionally includes a plurality of integrated circuits (ICs), each IC includes an ionizing radiation exposure sensor communicatively coupled to the controller circuit, and the ICs are fabricated using different IC processes.

In example 21, the apparatus of examples 1-20 optionally includes a memory communicatively coupled to the controller circuit and configured to store an indication of the non-SEU effect, and a communication circuit communicatively coupled to the controller circuit and configured to communicate with an external unit, and wherein the controller circuit is configured to communicate the indication of the non-SEU effect to the external unit.

In example 22, the apparatus of examples 1-21 optionally includes a plurality of ionizing radiation exposure sensors. The ionizing radiation exposure sensors are disposed with varying orientations to detect exposure to varying orientations of ionizing radiation.

In example 23, the apparatus of examples 1-22 is optionally included in at least one of a CFM device, a neural stimulation device, a drug delivery device, or a diagnostic device.

Example 24can include, or optionally be combined with the subject matter of one or any combination of examples 1-23 to include subject matter such as a method comprising detecting exposure of a solid state electronic circuit of an implantable medical device to ionizing radiation, and generating an indication of a non-single-event-upset (non-SEU) effect to the solid state electronic circuit from the exposure to ionizing radiation.

In example 25, the detecting exposure to ionizing radiation of example 24 optionally includes detecting exposure using an accumulated ionizing radiation exposure sensor that generates the indication of a non-SEU effect to the solid state electronic circuit from the solid state electronic circuit's accumulated exposure to ionizing radiation.

In example 26, the detecting exposure to ionizing radiation of examples 24 and 25 optionally includes detecting exposure using an ionizing radiation dose rate sensor that generates the indication of a non-SEU effect to the solid state electronic circuit when the solid state electronic circuit is exposed to flux ionizing radiation that exceeds a flux ionizing radiation threshold.

In example 27, the methods of examples 24-26 optionally includes communicating historical data regarding a non-SEU effect to an external device.

In example 28, the methods of examples 24-27 optionally includes altering operation of the IMD according to the indication of the non-SEU effect to the solid state electronic circuit.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) can include one or more of the features, structures, methods, or combinations thereof described herein. For example, a cardiac monitor or a cardiac stimulator can be implemented to include one or more of the advantageous features and/or processes described below. It is intended that such a monitor, stimulator, or other implantable or partially implantable device need not include all of the features described herein, but can be implemented to include selected features that provide for unique structures and/or functionality. Such a device can be implemented to provide a variety of therapeutic or diagnostic functions.

Figure 1:
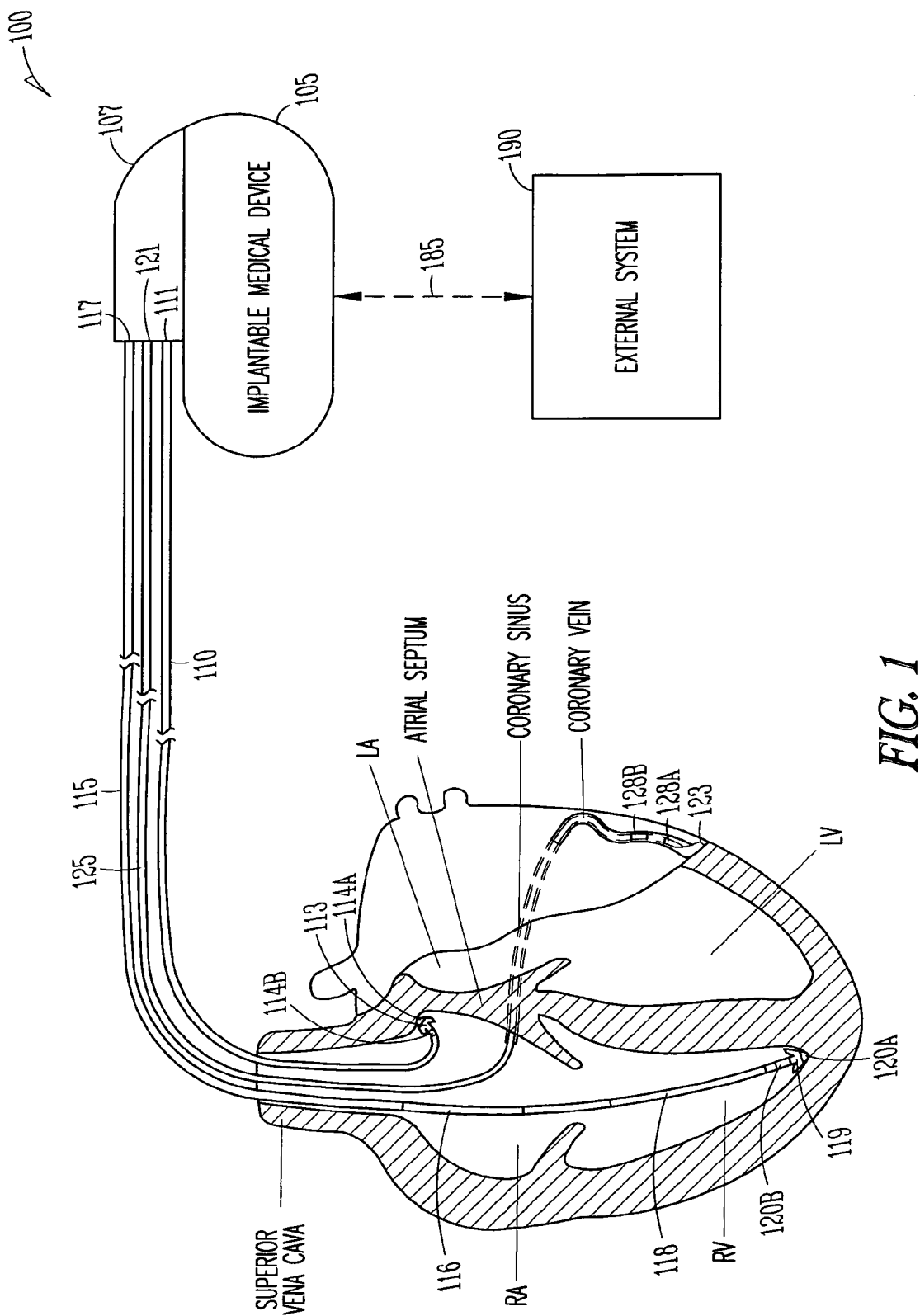
FIG. 1 is an illustration of an example of portions of a system that uses an IMD.

FIG. 1 is an illustration of portions of an example of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 can include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead can be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 can include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B can form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 can include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B can form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs can be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

Figure 2A:
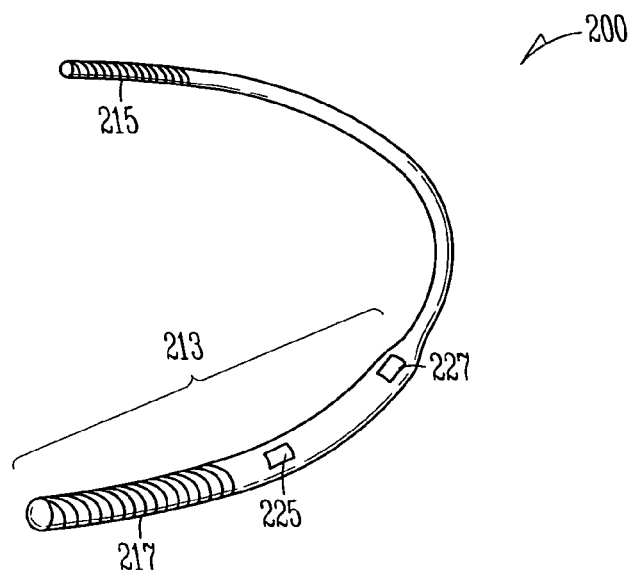
FIGS. 2A-B show an example of an IMD that does not use intravascular leads to sense cardiac signals.
Figure 2B:
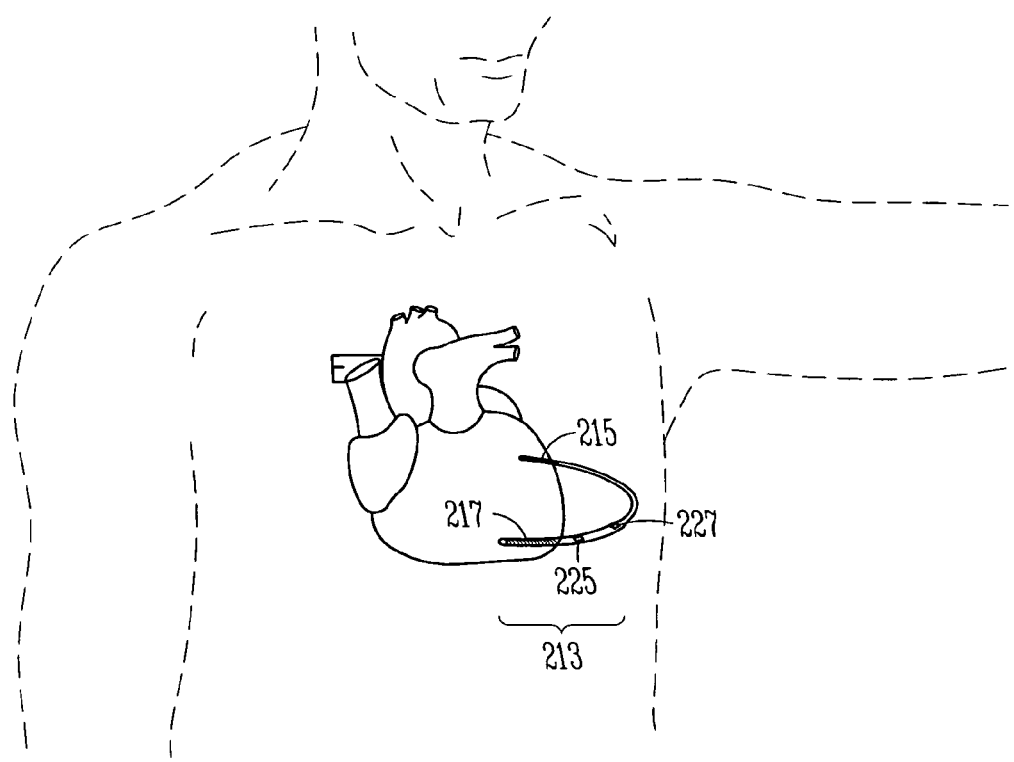

FIGS. 2A-B show an example of an IMD 200 that does not use intravascular leads to sense cardiac signals. FIG. 2A shows that the IMD 200 includes a thicker end 213 to hold the power source and circuits. The IMD 200 also includes electrodes 225 and 227 for remote sensing of cardiac signals. Cardioversion and/or defibrillation are provided through electrodes 215 and 217. FIG. 2B shows an example of the IMD 200 positioned within a patient.

An IMD can be exposed to diagnostic or therapeutic radiation doses that can negatively impact its operation. This type of radiation can be referred to as ionizing radiation (e.g., exposure to radioactive cobalt) to distinguish from radiation such as electromagnetic interference (EMI) that is typically dealt with in an IMD using EMI filters.

Despite the protection provided by the hermetically sealed can, ionizing radiation can penetrate to internal semiconductor devices. This penetrating radiation can cause a transient change or a permanent change (e.g., damage) to the operation of the device.

Some transient changes can include single event upsets (SEUs). A typical SEU corrupts memory (e.g., random access memory or RAM) resulting in a memory error. For example, an alpha particle impinging on a semiconductor substrate of a memory can generate electron-hole pairs that corrupt data stored as a charge on a capacitive element. The SEU can be resolved through memory checking during or after the exposure to the radiation. An example of systems and methods to detect and correct SEUs are described in Hoyme et al., U.S. Patent Publication No. 20050216063, titled "System and Method for Recovery from Memory Errors in Medical Device" which is incorporated herein by reference in its entirety.

The penetrating radiation can cause other changes (which are not SEUs) to semiconductor devices of the IMD. These non-SEU changes (transient or permanent) include changes to semiconductor operating parameters that are the result of accumulated total dose of the radiation or due to the radiation exposure dose rate.

An accumulated dose of ionizing radiation can damage the semiconductor lattice structures. This damage can lead to minority carrier disruptions that can particularly affect bipolar junction transistors (BJTs). The damage can also lead to trapped charge at junction interfaces as well as oxide trapped charge that primarily affect metal oxide semiconductor (MOS) transistors including p-channel MOS (PMOS) transistors and n-channel (NMOS) transistors which comprise complimentary metal oxide semiconductor (CMOS) transistors. The effect of the radiation on the semiconductor lattice structure can lead to shifts in operating parameters such as transistor threshold voltage, or transistor off-state current leakage. Also, CMOS devices can be used in the majority of circuits of an IMD, and thus CMOS device performance often determines overall IMD performance. Degradation of the performance of CMOS devices can be manifested as reduced IMD sensing capability and decreased IMD longevity.

By placing one or more circuits that monitor one or more semiconductor operating parameters within an IMD, the effect of total dose or dose rate on the semiconductor devices can be measured. Once the effect of the ionizing radiation on semiconductor devices has been measured, the IMD can implement one or more counteractions to address the radiation effect.

Figure 3:
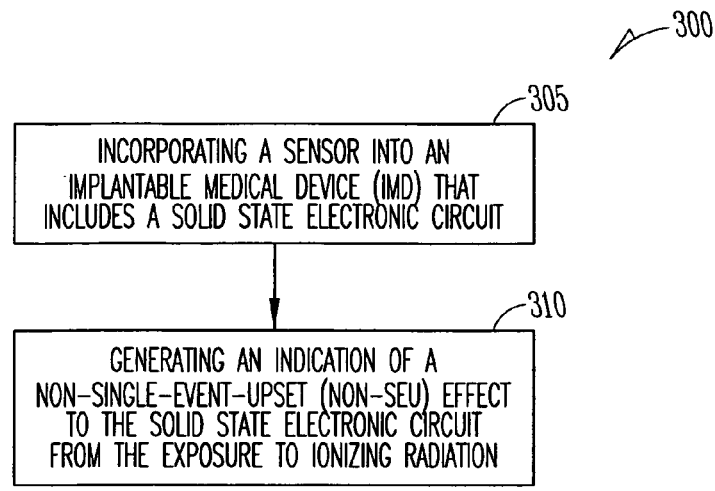
FIG. 3 is a flow diagram of an embodiment of a method to detect non-SEU effects of ionizing radiation on an IMD.

FIG. 3 is a flow diagram of an embodiment of a method 300 to detect non-SEU effects of ionizing radiation on an IMD. At block 305, a sensor is incorporated into an IMD. The IMD includes a solid state electronic circuit and the sensor detects exposure of the solid state electronic circuit to ionizing radiation. The solid state electronic circuit can provide a function of the IMD, or can be a multi-function integrated circuit (IC). At block 310, an indication is generated of a non-SEU effect to the solid state electronic circuit from the exposure to ionizing radiation.

Figure 4:
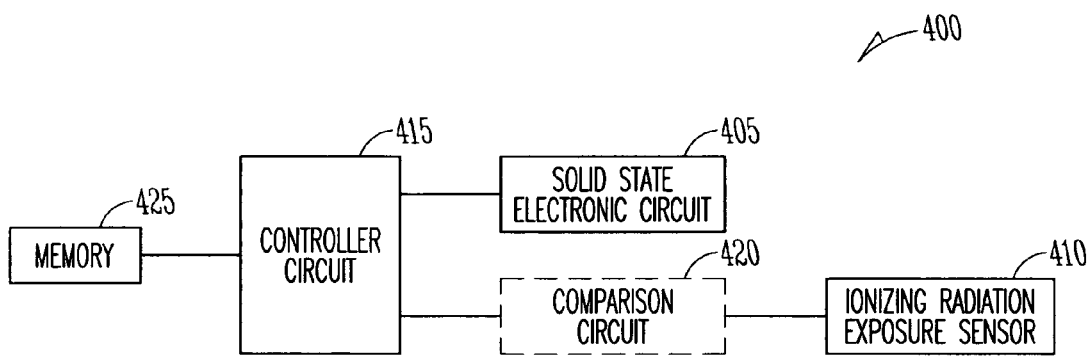
FIG. 4 is a block diagram of an embodiment of portions of an IMD.

FIG. 4 is a block diagram of an embodiment of portions of an IMD 400. The IMD 400 includes a solid state electronic circuit 405 and a sensor 410. The sensor is configured to detect an exposure of the solid state electronic circuit to ionizing radiation, and to generate an indication (e.g., an electrical sensor signal) of a non-SEU effect to the solid state electronic circuit from the exposure to ionizing radiation. In some examples, the IMD 400 includes a controller circuit 415 communicatively coupled to the ionizing radiation exposure sensor 410. The communicative coupling allows the controller circuit 415 to exchange electrical signals with the ionizing radiation exposure sensor 410 even though intervening circuitry can be present. The controller circuit 415 quantifies the effect to the solid state electronic circuit from the indication generated by the ionizing radiation exposure sensor. In some examples, the solid state electronic circuit 405 is included in the controller circuit 415.

The controller circuit 415 can include a digital signal processor, application specific integrated circuit (ASIC), microprocessor, or other type of processor, interpreting or executing instructions in software or firmware. The controller circuit 415 can include any combination of hardware, firmware, or software. In some examples, the controller circuit 415 can include a state machine or sequencer that is implemented in hardware circuits. The controller circuit 415 can include one or more modules to perform the functions described herein. A module can include software, hardware, firmware or any combination thereof. For example, a module can include instructions in software executing on the controller circuit 415. Multiple functions can be performed by one or more modules.

Figure 5A:
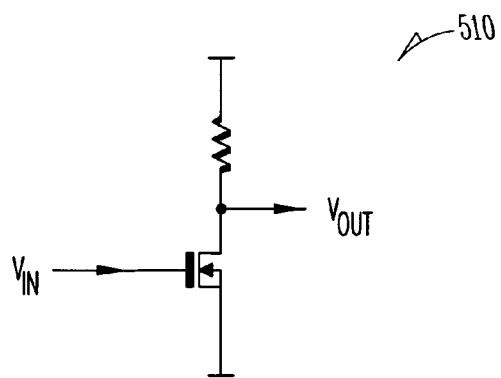
FIG. 5A shows an example of an ionizing radiation exposure sensor.
Figure 5B:
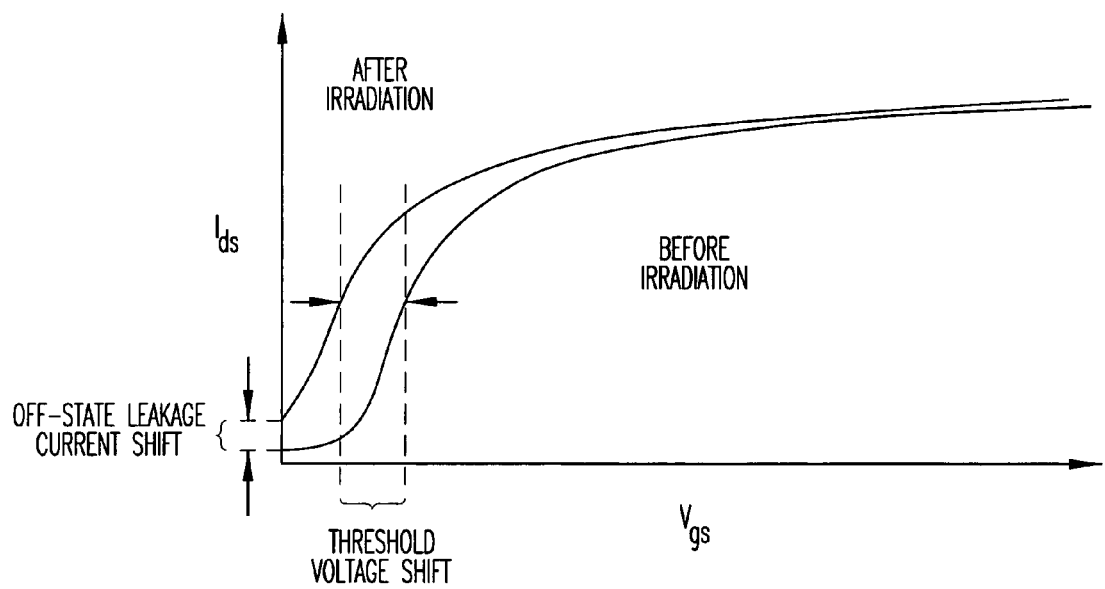
FIG. 5B shows an example of conceptual voltage-current curves for an NMOS transistor before and after exposure to ionizing radiation.

In some examples, the ionizing radiation exposure sensor 410 includes a test transistor. FIG. 5A shows an example of an ionizing radiation exposure sensor 510 that includes a test NMOS transistor. FIG. 5B shows two conceptual (not real data) voltage-current (VI) curves for an NMOS transistor before and after exposure to ionizing radiation. The curves show that the non-SEU effect from radiation exposure is expected to include an increase in off-state leakage current and a decrease in threshold voltage. Because of the decrease in drain-source current ($I_{ds}$) shown in the curves, the circuit of FIG. 5A will have a decrease in $V_{out}$ for a given $V_{in}$. Thus, the non-SEU effect can be detected from a shift in $V_{out}$.

In FIG. 5B, the curves illustrate a non-SEU that results in a decrease in threshold voltage (i.e., a shift to the left). The non-SEU effect can be an increase in threshold voltage (i.e., a shift to the right of the curve). Which way the threshold voltage shifts depends on the total radiation dose. For NMOS transistors, the threshold voltage decreases when the total radiation dose is high enough to cause oxide trapped charge to dominate over the interface trapped charge, and the threshold voltage increases when the interface trapped charge dominates over the oxide trapped charge. For PMOS transistors, the threshold voltage decreases regardless of whether the oxide trapped charge or the interface trapped charge dominates.

To monitor the operating parameters of the test transistor, $V_{in}$ can be ramped using a digital to analog (D/A) converter. Increasing digital values are provided to the input of the D/A converter (e.g., by the controller circuit 415) to generate a ramping analog voltage for $V_{in}$. The resulting $V_{out}$ of the test transistor can be monitored using an A/D converter. A D/A converter at $V_{in}$ and a A/D converter at $V_{out}$ allows VI operating curves such as those shown in FIG. 5B to be created by the IMD 400 in FIG. 4.

In some examples, the IMD 400 includes a comparison circuit 420 communicatively coupled to the ionizing radiation exposure sensor 410 and the controller circuit 415. The comparison circuit 420 compares one or more values of the operating curve to one or more operating curve threshold values and provides an indication (e.g., a change in a digital logic level at its output) to the controller circuit 415 when the operating curve value is shifted by more than the operating curve threshold value. In some examples, self-referencing is used in the comparison. In an example of self-referencing, the controller circuit 415 stores one or more operating curve values in a register or memory area at a specified point in time, such as at a pre-implant time. The comparison circuit 420 provides an indication when a current monitored operating curve value differs from the stored value by more than a specified threshold value.

In some examples, the circuit of FIG. 5A can be used together with radiation-hardened dedicated hardware to develop the ramp test voltages upon command of controller circuit 415. Fixed comparator levels can be used to detect quantized parametric threshold shifts without using radiation susceptible pulse generator hardware such as an A/D converter.

The controller circuit 415 alters operation of the IMD 400 if the comparison circuit 420 indicates a shift in an operating curve of the test transistor after exposure to radiation. An example of altering operation of the IMD 400 includes deactivating features of the IMD 400 that are associated with use of the solid state electronic circuit 405. In some examples, the IMD 400 includes a memory 425 integral to, or communicatively coupled to, the controller circuit 415. The memory 425 includes a read only memory (ROM) area. When an indication of a non-SEU effect is received from the comparison circuit, the controller circuit 415 can then transition the apparatus to a mode where the controller circuit 415 only executes program instructions that are included in the ROM. In certain examples, the instructions in ROM implement a device failure mode that provides reduced device functionality (e.g., a safety mode).

Another example of altering operation of the IMD 400 in response to a non-SEU effect includes deactivating a microprocessor used for full-functionality program execution and activating dedicated hardware in controller circuit 415 that provides reduced functionality. The reduced functionality can include cardioversion/defibrillation shock therapy and/or support pacing. Descriptions of devices and methods that continue to provide tachyarrhythmia shock therapy in the presence of system faults are found in Stubbs et al., "System and Method for Providing Tachyarrhythmia Therapy by an Implantable Device in Presence of System Faults, U.S. Patent Application Publication No. 20060253158, filed May 5, 2005, which is incorporated herein in its entirety. Descriptions of devices and methods that continue to provide support pacing therapy in the presence of system faults are found in Stubbs et al., "System and Method for Providing Bradycardia Therapy by an Implantable Device in Presence of System Faults, U.S. Patent Application Publication No. 20060253009, filed May 5, 2005, which is incorporated herein in its entirety.

In some examples, the ionizing radiation exposure sensor 410 includes a test field effect transistor (FET), such as a metal oxide semiconductor field effect transistor (MOSFET), and the comparison circuit 420 indicates a shift in drain-source current for a specified gate-source voltage applied to the test MOSFET.

In some examples, the ionizing radiation exposure sensor 410 includes a test junction diode, such as a PN junction diode or a Schottky junction diode. The comparison circuit 420 provides an indication to the controller circuit 415 if an operating curve of the test junction diode is shifted. The controller circuit 415 can be configured to alter operation of the IMD 400 if the comparison circuit 420 indicates a shift in an operating curve of the test junction diode after exposure to radiation.

In some examples, the ionizing radiation exposure sensor 410 includes a test amplifier circuit that includes a bipolar junction transistor. To monitor operation of the amplifier circuit, a specified input signal is provided to the amplifier input and the output signal is monitored to determine the signal gain. As with the NMOS circuit, the input signal can be provided by a D/A converter and the output signal can be monitored using an A/D converter. The comparison circuit provides an indication when there is a shift in signal gain of the test amplifier circuit. The controller circuit 415 alters operation of the IMD 400 if the comparison circuit 420 indicates a shift in signal gain of the test amplifier circuit after exposure to radiation.

The test transistor circuit of FIG. 5A is an example of an accumulated ionizing radiation exposure sensor. An accumulated ionizing radiation exposure sensor generates the indication of a non-SEU effect to the solid state electronic circuit from the solid state electronic circuit's accumulated exposure to ionizing radiation. For the sensor in FIG. 5A, the indication is the shift in $V_{out}$. This type of sensor can be referred to as a dosimeter.

Another type of suitable ionizing radiation exposure sensor is a dose rate sensor. This type of sensor generates the indication of a non-SEU effect to the solid state electronic circuit from the solid state electronic circuit's exposure to high flux ionizing radiation, such as when the solid state circuit is exposed to flux ionizing radiation that exceeds a predetermined flux ionizing radiation threshold. An ionizing radiation dose rate sensor can be referred to as a fluximeter.

Figures 6, 7:
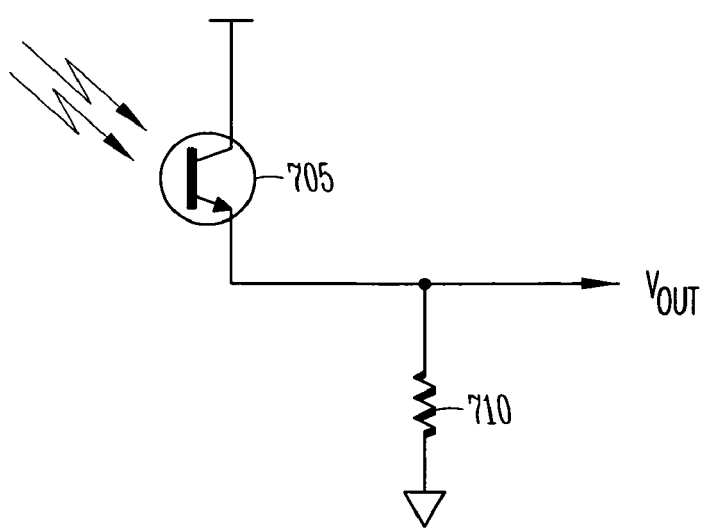
FIG. 6 shows an example of an ionizing radiation dose rate sensor.
FIG. 7 shows another example of an ionizing radiation dose rate sensor.

FIG. 6 shows an example of an ionizing radiation dose rate sensor 600 that includes a diode 605, such as a photo diode or a junction diode. During exposure to ionizing radiation, the diode 605 produces a current that produces a measurable voltage $V_{out}$ across resistor 610. The indication of exposure to the ionizing radiation can be when $V_{out}$ exceeds a specified voltage threshold.

FIG. 7 shows another example of an ionizing radiation dose rate sensor that includes a bipolar junction transistor (BJT) 705. The base of the BJT is floating and is arranged so that ionizing radiation is incident on the base creating electron-hole pairs. The electron-hole pairs create emitter to collector current that produces a measurable voltage $V_{out}$ across resistor 710.

It should be noted that the test circuits are also susceptible to the ionizing radiation. This susceptibility should be kept in mind when designing the test circuits and when choosing appropriate threshold shifts that determine a non-SEU effect. In some examples, the ionizing radiation exposure sensor 410 of FIG. 4 includes both an accumulated ionizing radiation exposure sensor and an ionizing radiation dose rate sensor. The controller circuit 415 blanks the indication from the accumulated ionizing radiation exposure sensor when the radiation dose rate sensor indicates high flux radiation. This reduces the chance of an erroneous indication from the accumulated ionizing radiation exposure sensor during detected high flux radiation.

In some examples, the solid state electronic circuit 405 is an IC. The IC can be a multi-functional IC. The ionizing radiation exposure sensor 410 monitors at least one operating parameter of the IC and indicates a shift in the first operating parameter of the IC. The controller circuit 415 modifies a second operating parameter of the IC to accommodate the shift in the first operating parameter. As an illustrative example, if the first operating parameter is the operating curve of a transistor or transistors, the controller circuit 415 can modify a supply voltage for the transistors, such as by reducing the voltage supply or switching in a different supply voltage for the transistors. If the voltage supply is changed, the controller circuit 415 can recalculate the useful life of the IMD battery based on the adjusted supply voltage.

In another example, if the first operating parameter is the operating curve of a transistor, the controller circuit 415 can modify a detection threshold (e.g., a comparator threshold) for a signal output from the transistor. In yet another example, if the first operating parameter is signal gain of an amplifier, dedicated on-board calibration hardware can be used to recalibrate one or more amplifiers in order to recover any lost signal gain.

In some examples, the IMD 400 includes a plurality of solid state electronic circuits disposed at a plurality of different locations in the IMD 400. Each location can include a solid state electronic circuit that performs a function different from a solid state electronic circuit at another location. The IMD 400 also includes a plurality of ionizing radiation exposure sensors disposed at the different locations, with at least one ionizing radiation exposure sensor 410 at each location. The controller circuit 415 deactivates a function of the apparatus when an ionizing radiation exposure sensor 410 indicates a permanent non-SEU effect to the solid state electronic circuit 405 at a location corresponding to the function.

Radiation therapy can be omni-directional (e.g., a radioactive solid source) or can have a specific direction and radiation pattern (e.g., a beam from a linear accelerator). For ionizing radiation from a beam source, proper orientation of the radiation monitoring structure and/or circuit is useful to ensure detection. The spatial relationship between the IMD 400 and the penetrating radiation depends on the type of radiation therapy, the patient orientation, the IMD orientation, and the radiation monitor structure orientation within the IMD. In some examples, the IMD 400 includes a plurality of ionizing radiation exposure sensors. The ionizing radiation exposure sensors are disposed with varying orientations to detect exposure to varying orientations of ionizing radiation.

In certain examples, the ionizing radiation exposure sensors include MOS transistors that can be oriented so that their channels are mutually orthogonal to provide directional coverage. In certain examples, the ionizing radiation exposure sensors include MOS transistors and a monitoring circuit to measure leakage current from parasitic diodes within the MOS transistors. The monitoring circuit measures both the source-drain leakage current in addition to leakage current from the parasitic source-body or drain-body diodes. Measuring the source-drain current provides device monitoring in a first axis direction (the lateral axis to the IC) while monitoring leakage current from the source-body or drain-body parasitic diodes provides device monitoring in a second axis direction (the normal axis to the IC). This concept can be expanded to provide monitoring in a third axis direction by turning the transistors sideways to one another. Operating the MOS transistors in weak-inversion can increase their sensitivity to ionizing radiation.

Typically, all of the circuits in the IMD 400 are subject to approximately the same total radiation dose. However, use of multiple monitoring circuits in the IMD 400 can provide comprehensive monitoring of the effects of the ionizing radiation. The solid state electronic circuits in the IMD can have different structures that respond differently to similar doses of radiation. In some examples, the IMD 400 includes a plurality of solid state electronic circuits disposed at a plurality of different locations in the apparatus and a plurality of ionizing radiation exposure sensors disposed at the different locations. In some examples, the plurality of solid state electronic circuits includes a plurality ICs. Each IC includes an ionizing radiation exposure sensor communicatively coupled to the controller circuit 415. Some of the ICs can be fabricated using different IC processes.

The ionizing radiation exposure sensors can include different circuit structures to monitor different operating parameters of one or more solid state circuits. The controller circuit 415 quantifies the effect to the solid state electronic circuits using the different monitored operating parameters.

A non-exhaustive list of circuits that can be used in the ionizing radiation exposure sensors include a PN junction diode test circuit, a schottky junction diode test circuit, an N-channel MOSFET test circuit, a P-channel MOSFET test circuit, an NPN bipolar junction transistor test circuit, and a PNP bipolar junction transistor test circuit. Other circuits and techniques which measure charge can be used. The monitoring circuits generate an indication of a non-SEU effect to the solid state electronic circuit from the exposure to ionizing radiation. The controller circuit 415 quantifies the effect to the solid state electronic circuit from indications provided by the monitoring circuits, such as by determining a shift in an operating curve of a monitoring circuit. The controller circuit 415 can alter operation of the IMD 400 according to the indications.

Figure 8:
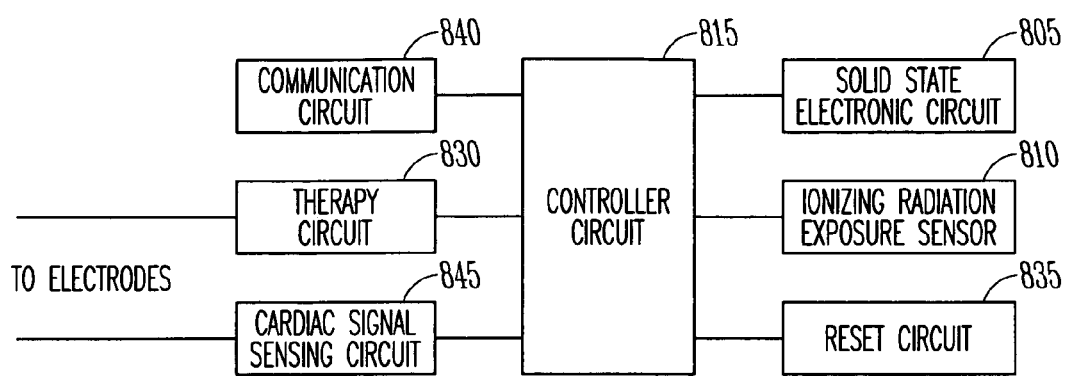
FIG. 8 is a block diagram of another embodiment of portions of another IMD.

FIG. 8 is a block diagram of another embodiment of portions of an IMD 800. The IMD 800 includes a solid state electronic circuit 805, an ionizing radiation exposure sensor 810, and a controller circuit 815. The IMD 800 is a CFM device and includes a therapy circuit 830. In some examples, the therapy circuit 830 provides pacing therapy via implantable electrodes. When an indication of a non-SEU effect is received, the controller circuit 815 transitions the IMD 800 to a mode that provides pacing therapy to a ventricle when a V-V interval exceeds a specified ventricular interval without timing the pacing of the ventricle from an atrial cardiac event, and provides pacing therapy without regard to any intrinsic cardiac depolarization event occurring in the ventricle (e.g., the NASPE/BPEG-defined VOO mode). In some examples, the controller circuit 815 adjusts therapy calibration values when an indication of a non-SEU effect is received.

In some examples, the IMD 800 includes a reset circuit 835 communicatively coupled to the controller circuit 815. The reset circuit 835 provides a systematic reset to the IMD 800 which makes sure the IMD 800 is brought to known state in a systematic fashion. The controller circuit 815 initiates a device reset according to the indication of the non-SEU effect. In certain examples, the reset circuit 835 sequentially powers down and then powers up the solid state electronic circuit. This can resolve some transient non-SEU events. For example, resetting the power supplies to the solid state electronic circuit can resolve a latch-up condition in CMOS devices.

In some examples, the IMD 800 includes a communication circuit 840 to communicate with an external unit or system. The controller circuit 815 stores the indication of a non-SEU effect in memory and communicates indication of the non-SEU effect to the external unit. In some examples, indications of non-SEU events are stored as a log in memory of the IMD 800. A log entry can include the time and date the controller circuit 815 received the indication or other contextual information of the non-SEU effect. Reading out the log from IMD memory and communicating historical data regarding a non-SEU effect to an external device can help in troubleshooting the IMD 800.

In some examples, the IMD 800 includes one or more sensing features and the ionizing radiation exposure sensor 810 is an ionizing radiation dose rate sensor. An example of a sensing feature is a cardiac signal sensing circuit 845. The cardiac signal sensing circuit 845 provides an electrical signal representative of an intrinsic cardiac signal. The controller circuit 815 blanks one or more sensing features of the IMD 800 when the ionizing radiation dose rate sensor detects high flux ionizing radiation. Blanking the sensing feature can include ignoring sensed signals, or disconnecting or enabling circuits that provide the signals. In certain examples, the blanking includes blanking of an accumulated ionizing radiation exposure sensor. In certain examples, the blanking of sensing features is done via programming of the IMD 800 by an external device.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical apparatus comprising:
a plurality of solid state electronic circuits disposed at a plurality of different locations in the apparatus;
a plurality of ionizing radiation exposure sensors disposed at the different locations and configured to generate an indication of a non-single-event-upset (non-SEU) effect to the correspondingly located solid state electronic circuit from an exposure to ionizing radiation, wherein an ionizing radiation exposure sensor includes at least one circuit structure to detect the exposure to ionizing radiation by monitoring at least one operating parameter of the solid state circuit, and wherein the ionizing radiation exposure sensors respectively monitor at least two different types of operating parameters of respectively correspondingly located solid state circuits; and
a controller circuit communicatively coupled to the ionizing radiation exposure sensors, wherein the controller circuit is configured to quantify the effect to the solid state electronic circuits using the different monitored operating parameters.

2. The apparatus of claim 1, wherein the controller circuit is configured to alter operation of the apparatus according to the indication of the non-SEU effect.

3. The apparatus of claim 1, including:
a plurality of solid state electronic circuits configured to perform different functions at a plurality of different locations in the apparatus; and
wherein the controller circuit is configured to inhibit or deactivate a function of the apparatus when an ionizing radiation exposure sensor indicates a permanent non-SEU effect to the solid state electronic circuit at a location corresponding to the function.

4. The apparatus of claim 1, including a comparison circuit communicatively coupled to an ionizing radiation exposure sensor and the controller circuit, wherein the ionizing radiation exposure sensor includes a test transistor, and wherein the controller circuit is configured to alter operation of the apparatus if the comparison circuit indicates a shift in an operating curve of the test transistor after exposure to radiation.

5. The apparatus of claim 4, wherein the test transistor includes a test field effect transistor (FET), and wherein the comparison circuit is configured to indicate a shift in drain-source current for a specified gate-source voltage applied to the test FET.

6. The apparatus of claim 1, including a comparison circuit communicatively coupled to an ionizing radiation exposure sensor and the controller circuit, wherein the ionizing radiation exposure sensor includes a test junction diode, and wherein the controller circuit is configured to alter operation of the apparatus if the comparison circuit indicates a shift in an operating curve of the test junction diode after exposure to radiation.

7. The apparatus of claim 6, wherein the ionizing radiation exposure sensor includes a test amplifier circuit that includes a bipolar junction transistor, and wherein the comparison circuit is configured to indicate a shift in signal gain of the test amplifier circuit for a specified input signal applied to the amplifier circuit.

8. The apparatus of claim 1, wherein the radiation exposure sensors include at least one of:
a PN junction diode test circuit;
a schottky junction diode test circuit;
an N-channel FET test circuit;
a P-channel FET test circuit;
an NPN bipolar junction transistor test circuit; and
a PNP bipolar junction transistor test circuit.

9. The apparatus of claim 1, wherein an ionizing radiation exposure sensor comprises an accumulated ionizing radiation exposure sensor and is configured to generate the indication of a non-SEU effect to the solid state electronic circuit from the solid state electronic circuit's accumulated exposure to ionizing radiation.

10. The apparatus of claim 9, wherein the apparatus includes an ionizing radiation dose rate sensor communicatively coupled to the controller circuit, and wherein the controller circuit is configured to blank the indication from the accumulated ionizing radiation exposure sensor when the radiation dose rate sensor indicates that flux ionizing radiation exceeds a flux ionizing radiation threshold.

11. The apparatus of claim 1, wherein an ionizing radiation exposure sensor is an ionizing radiation dose rate sensor configured to generate the indication of a non-SEU effect to the solid state electronic circuit from the solid state electronic circuit's exposure to flux ionizing radiation that exceeds a flux ionizing radiation threshold.

12. The apparatus of claim 11, wherein the apparatus comprises a cardiac function management (CFM) device, and wherein the controller circuit is configured to blank any sensing features of the CFM device when the ionizing radiation dose rate sensor detects high flux ionizing radiation.

13. The apparatus of claim 11, wherein the ionizing radiation dose rate sensor includes at least one of a junction diode or a bipolar junction transistor.

14. The apparatus of claim 1, wherein the apparatus is a CFM device, wherein the controller circuit is configured to, according to the indication of the non-SEU effect, transition the CFM device to a mode that provides pacing therapy to a ventricle when a V-V interval exceeds a specified ventricular interval without timing the pacing of the ventricle from an atrial cardiac event, and that provides pacing therapy without regard to any intrinsic cardiac depolarization event occurring in the ventricle.

15. The apparatus of claim 1, including a read only memory (ROM) communicatively coupled to the controller circuit, and wherein the controller circuit is configured to, according to the indication of the non-SEU effect, transition the apparatus to a mode where the controller circuit only performs program instructions that are included in the ROM.

16. The apparatus of claim 1, including a reset circuit communicatively coupled to the controller circuit, and wherein the controller circuit is configured to initiate a reset to the apparatus according to the indication of the non-SEU effect.

17. The apparatus of claim 1,
wherein a solid state electronic circuit comprises an integrated circuit (IC),
wherein an ionizing radiation exposure sensor is configured to indicate a shift in a first operating parameter of the IC, and
wherein the controller circuit is configured to modify a second operating parameter of the IC to accommodate the shift in the first operating parameter.

18. The apparatus of claim 1, including a plurality of integrated circuits (ICs), each IC including including at least one of the plurality of ionizing radiation exposure sensors communicatively coupled to the controller circuit, and wherein the ICs are fabricated using different IC processes.

19. The apparatus of claim 1, including:
a memory communicatively coupled to the controller circuit and configured to store an indication of the non-SEU effect; and
a communication circuit communicatively coupled to the controller circuit and configured to communicate with an external unit, and wherein the controller circuit is configured to communicate the indication of the non-SEU effect to the external unit.

20. The apparatus of claim 1, wherein the ionizing radiation exposure sensors are disposed with varying orientations to detect exposure to varying orientations of ionizing radiation.

21. The apparatus of claim 1, wherein the implantable medical apparatus is included in at least one of a CFM device, a neural stimulation device, a drug delivery device, or a diagnostic device.

22. The apparatus of claim 1, including a memory communicatively coupled to the controller circuit and configured to store an operating curve value for at least one ionizing radiation exposure sensor circuit, and wherein the controller circuit is configured to quantify the effect of ionizing radiation to a correspondingly located solid state electronic circuit using a comparison of a monitored operating curve value to the stored operating curve value.

23. A method comprising:
detecting exposure of a plurality of solid state electronic circuits disposed at different locations of an implantable medical device to ionizing radiation by respectively monitoring at least two different types of operating parameters of respectively located solid state circuits;
quantifying the effect to the solid state electronic circuits to the ionizing radiation using the different monitored operating parameters; and
generating an indication of a non-single-event-upset (non-SEU) effect to the solid state electronic circuits from the exposure to ionizing radiation.

24. The method of claim 23, wherein detecting exposure to ionizing radiation includes detecting exposure using an accumulated ionizing radiation exposure sensor that generates the indication of a non-SEU effect to the solid state electronic circuit from the solid state electronic circuit's accumulated exposure to ionizing radiation.

25. The method of claim 23, wherein detecting exposure to ionizing radiation includes detecting exposure using an ionizing radiation dose rate sensor that generates the indication of a non-SEU effect to the solid state electronic circuit when the solid state electronic circuit is exposed to flux ionizing radiation that exceeds a flux ionizing radiation threshold.

26. The method of claim 23, including communicating historical data regarding a non-SEU effect to an external device.

27. The method of claim 23, including altering operation of the IMD according to the indication of the non-SEU effect to the solid state electronic circuit.

* * * * *

UNITED STATES PATENT AND TRADEMARK OFFICE
CERTIFICATE OF CORRECTION

| | | |
|---|---|---|
| PATENT NO. | : 7,935,936 B2 | |
| APPLICATION NO. | : 12/361935 | |
| DATED | : May 3, 2011 | |
| INVENTOR(S) | : Jeffrey E. Stahmann et al. | |

It is certified that error appears in the above-identified patent and that said Letters Patent is hereby corrected as shown below:

In column 1, line 9, delete "it" and insert -- its --, therefor.

In column 3, line 54, delete "24can" and insert -- 24 can --, therefor.

In column 15, line 36, in Claim 18, delete "including including" and insert -- including --, therefor.

Signed and Sealed this
Twenty-first Day of June, 2011

David J. Kappos
*Director of the United States Patent and Trademark Office*